(12) United States Patent
Smisson, III et al.

(10) Patent No.: US 7,713,236 B2
(45) Date of Patent: *May 11, 2010

(54) AIRTRAP

(75) Inventors: Hugh F. Smisson, III, Macon, GA (US); Richard G. Cartledge, Hollywood, FL (US); John M. Iaconis, Monroeville, PA (US); Michael L. Koltz, Ormond Beach, FL (US); Bradford J. Rainier, DeLand, FL (US)

(73) Assignee: Smisson-Cartledge Biomedical LLC, Macon, GA (US)

(*) Notice: Subject to any disclaimer, the term of this patent is extended or adjusted under 35 U.S.C. 154(b) by 1320 days.

This patent is subject to a terminal disclaimer.

(21) Appl. No.: 11/115,452

(22) Filed: Apr. 27, 2005

(65) Prior Publication Data

US 2006/0211986 A1    Sep. 21, 2006

Related U.S. Application Data

(63) Continuation of application No. 11/082,260, filed on Mar. 17, 2005, now Pat. No. 7,563,248.

(51) Int. Cl.
*A61M 1/00* (2006.01)
(52) U.S. Cl. ..................................... 604/122
(58) Field of Classification Search .................. 604/31, 604/65–67, 113, 122–124, 128–129, 133
See application file for complete search history.

(56) References Cited

U.S. PATENT DOCUMENTS 3,590,215 A    6/1971  Anderson et al.
4,137,160 A *  1/1979  Ebling et al. .................. 95/259
4,370,983 A    2/1983  Lichtenstein
4,475,901 A   10/1984  Kraegen et al.
4,537,561 A    8/1985  Xanthopoulos
4,747,826 A    5/1988  Sassano (Continued)

FOREIGN PATENT DOCUMENTS

WO    WO97/21456 A1    6/1997

OTHER PUBLICATIONS

U.S. Appl. No. 11/835,095, filed Aug. 7, 2007, Smisson III et al.

(Continued)

*Primary Examiner*—Nicholas D Lucchesi
*Assistant Examiner*—Rebecca E Eisenberg
(74) *Attorney, Agent, or Firm*—Sutherland Asbill & Brennan LLP

(57)    ABSTRACT

The present invention relates to a system for increasing the temperature of a fluid being infused into a patient's body while the infusion is taking place. The present invention also provides for improved monitoring of air in the infusion system such to prevent the introduction of air into the patient's body receiving the fluid infusion. The present invention also provides for a system pump which provides a variable flow rate that serves a vast amount of infusion needs and purposes. A disposable cartridge in accordance with the present invention will allow for the efficient transfer of heat energy to the fluid being infused into the patient's body. The cartridge will further ensure that deleterious amounts of air will not be introduced into the patient's body.

18 Claims, 10 Drawing Sheets

U.S. PATENT DOCUMENTS

| | | | |
|---|---|---|---|
| 4,806,135 A * | 2/1989 | Siposs | 96/212 |
| 4,847,470 A | 7/1989 | Bakke | |
| 4,874,359 A | 10/1989 | White et al. | |
| 4,981,467 A | 1/1991 | Bobo, Jr. et al. | |
| 5,061,241 A | 10/1991 | Stephens, Jr. et al. | |
| 5,104,374 A | 4/1992 | Bishko et al. | |
| 5,125,069 A | 6/1992 | O'Boyle | |
| 5,181,910 A | 1/1993 | Scanlon | |
| 5,245,693 A | 9/1993 | Ford et al. | |
| 5,273,517 A | 12/1993 | Barone et al. | |
| 5,311,908 A | 5/1994 | Barone et al. | |
| 5,366,346 A | 11/1994 | Danby | |
| 5,381,510 A | 1/1995 | Ford et al. | |
| 5,385,540 A | 1/1995 | Abbott et al. | |
| 5,429,602 A | 7/1995 | Hauser | |
| 5,464,391 A | 11/1995 | De Vale | |
| 5,482,446 A | 1/1996 | Williamson et al. | |
| 5,514,095 A | 5/1996 | Brightbill et al. | |
| 5,573,502 A | 11/1996 | LeCocq et al. | |
| 5,586,085 A | 12/1996 | Lichte | |
| 5,590,654 A | 1/1997 | Prince | |
| 5,591,251 A | 1/1997 | Brugger | |
| 5,645,531 A | 7/1997 | Thompson et al. | |
| 5,656,027 A | 8/1997 | Ellingboe | |
| 5,746,719 A | 5/1998 | Farra et al. | |
| 5,782,805 A | 7/1998 | Meinzer et al. | |
| 5,800,387 A | 9/1998 | Duffy et al. | |
| 5,857,843 A | 1/1999 | Leason et al. | |
| 5,876,370 A | 3/1999 | Blomquist | |
| 6,074,363 A | 6/2000 | Beran et al. | |
| 6,117,342 A * | 9/2000 | Schnell et al. | 210/800 |
| 6,175,688 B1 | 1/2001 | Cassidy et al. | |
| 6,236,809 B1 | 5/2001 | Cassidy et al. | |
| 6,259,074 B1 | 7/2001 | Brunner et al. | |
| 6,270,478 B1 | 8/2001 | Mernoe | |
| 6,464,666 B1 | 10/2002 | Augustine et al. | |
| 6,475,178 B1 | 11/2002 | Krajewski et al. | |
| 6,480,257 B2 | 11/2002 | Cassidy et al. | |
| 6,622,542 B2 | 9/2003 | Derek et al. | |
| 6,719,779 B2 | 4/2004 | Daoud | |
| 6,775,473 B2 | 8/2004 | Augustine et al. | |
| 7,004,924 B1 | 2/2006 | Brugger et al. | |
| 2005/0022274 A1 | 1/2005 | Campbell et al. | |
| 2005/0209563 A1 | 9/2005 | Hopping et al. | |
| 2006/0211988 A1 | 9/2006 | Smisson, III et al. | |

OTHER PUBLICATIONS

U.S. Appl. No. 11/835,118, filed Aug. 7, 2007, Smisson III et al.
U.S. Appl. No. 11/835,125, filed Aug. 7, 2007, Smisson III et al.
U.S. Appl. No. 11/835,132, filed Aug. 7, 2007, Smisson III et al.

\* cited by examiner

AIRTRAP

This application is a continuation of U.S. patent application Ser. No. 11/082,260, filed on Mar. 17, 2005 now U.S. Pat. No. 7,563,248.

BACKGROUND OF THE INVENTION

1. Field of the Invention

The present invention is directed to warming fluid for infusion to a patient's body without damaging the fluid through exposure to increased temperature as well as preventing the introduction of air into the patient's body.

2. Background

Fluid required in treating a patient must often be stored in comparatively cool to cold temperatures with respect to the patient's body temperature. This often refrigerated storage is necessary to preserve the fluids in a state so the function and integrity of the fluid is maintained. Fluids such as blood and other bodily fluids are typically stored at hypothermic temperatures ranging from 2° to 20° Celsius. Therefore, when introducing fluids into the patient's body it is often necessary to heat the fluid to an appropriate temperature not only to prevent any rapid decrease in the patient's body temperature, but also to ensure that the fluid being introduced can function as needed. It is known that the injection of cold fluids into a patient's body can create a major source of conductive heat loss within the patient, often placing the patient at further risk by cooling, too quickly or, to a temperature where physiological damage can occur.

In heating or warming the fluid, however, care must be taken to ensure that the heating itself does not create a further complication. For instance, if blood is exposed to a temperature of above 45° Celsius hemolysis, the destruction or severe degradation, of the blood cells can occur. Likewise, if the fluid is heated too high and then introduced into the patient's body, physiological damage resulting from exposure to excessive temperatures such as burns or other such scarring can occur. Heating the fluid in bulk form usually requires the application of too intense a heat source in order to heat the entire fluid with any level of time efficiency. Likewise, heating the fluid over a prolonged period of time can lead to increased exposure of the material to the environment creating risks of contamination.

Getting the fluid into the patient requires adjustable flow so that the proper amount of fluid depending upon the need is provided to the patient. Combining the fluid delivery means with the proper and efficient heating of the fluid is crucial to the proper delivery of fluid to the patient. The prior art contains systems for warming fluids as they are infused into a patient. The manner in which the fluids are heated within these systems varies and can be accomplished via convection or conduction. An example of a system which poses clinical problems heats the fluid being delivered to the patient via exposure to a heated fluid, such as water. Such systems are usually cumbersome, require frequent cleaning, and can pollute the clinical environment through the introduction of an additional substance—the heating liquid. Such a system often places a conduit through a liquid such as water, which is then heated, and the fluid to be delivered to the patient is drawn through the conduit thereby increasing the temperature of the fluid to be delivered. Such a system can be deleterious to a sterile environment and may not be properly transported. Furthermore, these systems also have large mass which require significant power to heat that mass yielding a significant time to achieve that temperature, or achieve a stasis when a cold mass (like a bag of chilled fluid) is introduced.

Moreover, during some fluid infusion procedures it is beneficial to adjust the temperature of the patient's body either warmer or cooler. As such it is extremely beneficial to have an adjustable in-line fluid warming system so that the proper temperature can be regulated. In instances of massive or emergent fluid loss, it is often necessary to infuse extremely large amounts of fluid into the patient's body. In such instances, traditional fluid heating systems often place the fluid at risk by exposure to temperatures which could damage the fluid because the fluid must be heated so rapidly. Such problems remain largely unsolved by the art and need for better in-line fluid infusers is abundant.

When introducing fluid into a patient's body it is crucial that air not be introduced into the patient's body as well. Introduction of air or air bubbles into a patient's body can cause extremely deleterious effects. Air embolisms can occur if air accumulates in a patient's blood stream resulting in cardiac arrhythmias, stroke, or pulmonary infarct. Any of these potential infirmities can be life threatening and need to be minimized in situations where high volumes of bodily fluid are being infused. It is therefore extremely important that during infusion of bodily fluid that both the monitoring of air in the infusion system occurs to prevent introduction into the patient's body.

Devices in the prior art seeking to warm fluid for infusion into the body often suffer from very specific problems. For example, the heater system described in U.S. Pat. No. 3,590,215 issued to Anderson et al. uses regions of differing heat which the fluid encounters as it progresses through the system. Specifically, the heating element or elements described in Anderson et al. diminishes the heat in the material warming the fluid from a hottest temperature where the fluid enters the heat exchanger to a coolest temperature where the fluid exits the heat exchanger. Such a configuration not only makes it difficult to regulate the temperature of the fluid as the flow rate changes, but it also runs the risk of having to expose the fluid to temperatures above which the fluid should be exposed to, running the risk of damaging the fluid.

Likewise, the serpentine fluid flow path described in Anderson et al. creates the typical laminar type flow seen in most heat exchanger systems. For example, U.S. Pat. No. 5,245,693 to Ford et al. describes a serpentine flow pattern which is long compared to its width and wider compared to its depth. This type of flow is consistent with a non-turbulent laminar type flow path. A non-turbulent flow path requires additional heat energy to be introduced into the fluid system in order to increase the temperature of the fluid system uniformly to a desired temperature.

SUMMARY OF THE INVENTION

The present invention is a system for increasing the temperature of a fluid being infused into a patient's body while the infusion is taking place. Such a heating system is also referred to as an in-line heating infusion system. The present invention also provides for improved monitoring of air in the infusion system such to prevent the introduction of air into the patient's body receiving the fluid infusion. The present invention also provides for a system pump which provides a variable flow rate that serves a vast amount of infusion needs and purposes.

A disposable cartridge in accordance with the present invention will allow for the efficient transfer of heat energy to the fluid being infused into the patient's body. The cartridge will further ensure that deleterious amounts of air will not be introduced into the patient's body.

DETAILED DESCRIPTION OF THE INVENTION

Figure 1:
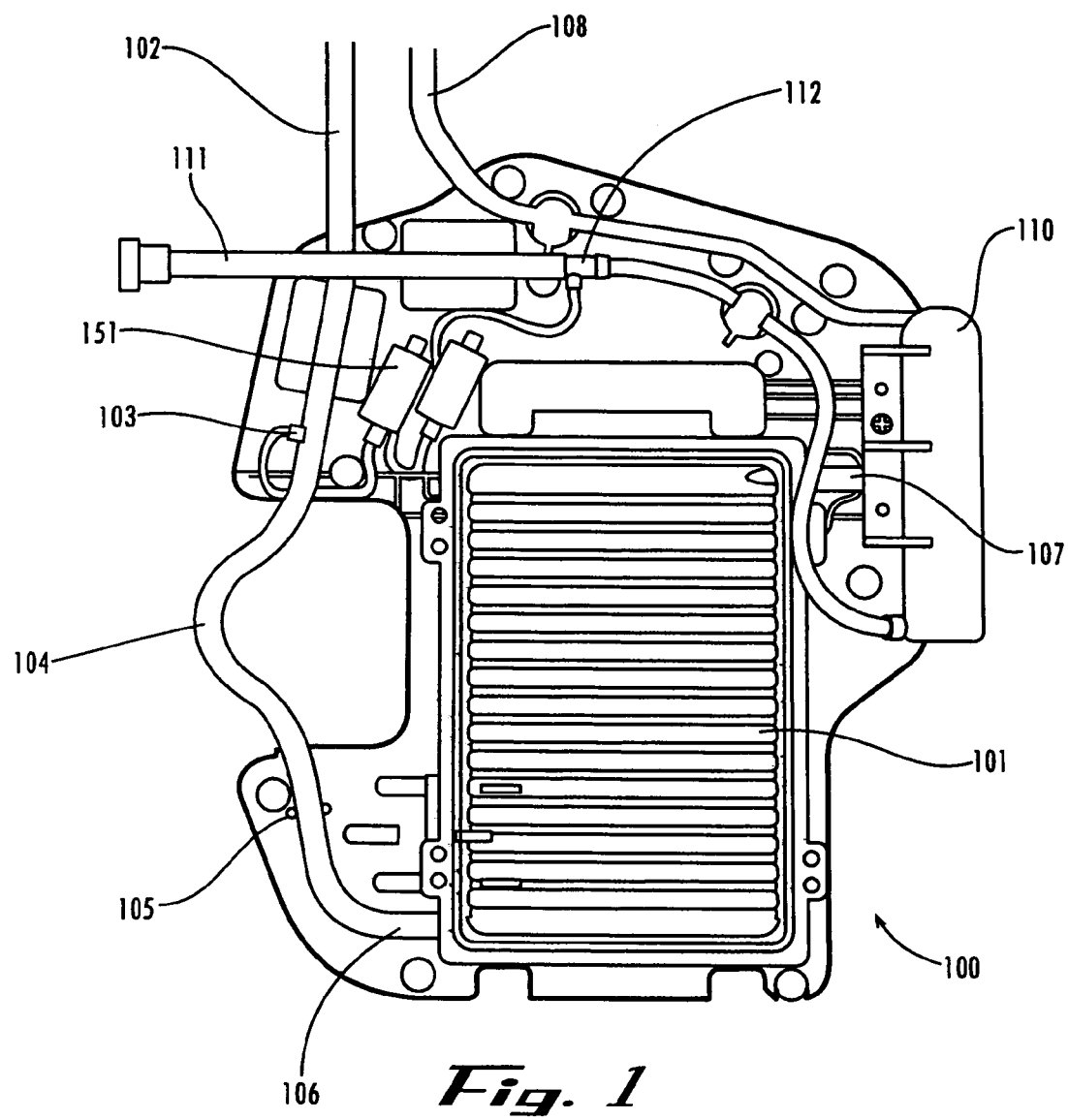
FIG. 1 is an elevation view of the internal elements of a disposable cartridge in accordance with the present invention.

The present invention contemplates a disposable heat exchange cartridge for use in fluid infusion into a patient's body. The disposable heat exchange cartridge is removably coupled to an infusion pump device which provides not only the energy or power required to covey heat to the fluid being infused, but also provides the flow generating pump and mechanisms for monitoring and regulating particular aspects of the fluid infusion system. In this description of the invention reference will be made to the embodiments shown in FIGS. 1-8 wherein like numerals are used to designate like parts throughout. FIGS. 1 and 2a-c describe a currently preferred embodiment of the present invention and should not be viewed as limiting.

One embodiment of the present invention is a disposable fluid infusion cartridge comprising a heat exchanger having upper and lower aspects and an internal heat exchange zone defined by a first and second plurality of overlapping fins, creating a substantially uniform flow path depth, wherein each fin has a ratio of height to width of at least 1:2, whereby fluid enters the lower aspect of the heat exchanger via a lower port and fills a lower flow cavity across the width of the heat exchange zone prior to flowing through the heat exchange zone and out an upper port at the upper aspect of the heat exchanger.

The disposable fluid infusion cartridge can further comprise an air-trap having upper and lower aspects, an inner surface, which receives the fluid from the heat exchanger, and further comprising a fluid flow disrupter and a purging mechanism for purging air from the air trap and preventing air from passing beyond the air trap. The disposable cartridge of this embodiment can have a ratio of the height of the fins to the width of the fins from about 1:2 to 1:50, preferably from about 1:4 to 1:25, and most preferably from about 1:5 to 1:10. The height of the fins in the present embodiment can be from about 0.25 inches to about 1 inch.

The disposable cartridge of the present embodiment can have a ratio of the flow path depth to the height of the fins from about 0.01:1 to about 1:1. The flow path of the heat exchange zone of the present embodiment can have a depth of about 0.01 inches to about 0.25 inches. Moreover, the distance between a first and second fin within the same plurality of fins can be from about 0.25 inches to about 0.5 inches. Also, the heat exchanger of the present invention can be comprised of two symmetric units fixed together, a single unit, or comprised of at least two units fixed together.

The air-trap of the present embodiment of a disposable fluid infusion system can be cylindrical wherein the air-trap is taller than it is wide. The air-trap of the present embodiment further comprises a fluid flow disrupter which extends from the inner surface of the lower aspect of the air-trap. Moreover, the purging mechanism can utilize an ultrasonic detection mechanism to monitor fluid volume in the air-trap. Likewise, the purging mechanism of the present embodiment can utilize a valve at a fluid output port and a valve at an air output port working in tandem to force air out the air output port as the volume of the fluid within the air-trap increases to a predetermined level. The air-trap of the present embodiment can effectively remove air when moved off its vertical axis up to 45°.

In another embodiment of the present invention the disposable infusion cartridge can comprise a heat exchanger comprising an enclosed uniform tortious flow path containing short segments of linear flow length, creating a ribbon of fluid, greater in width than the length of segments of linear flow length, for enhanced exposure to the inner surface of the heat exchanger and mixing of the fluid via non-laminar flow to enhance heat transfer within the fluid.

The disposable infusion cartridge of this embodiment can further comprise a cylindrical air-trap for removing air from the disposable cartridge comprising an upper and lower aspect and further comprising a fluid input port, a fluid output port, an air output port, and a fluid flow disrupter wherein the air-trap creates a vortex of fluid and the fluid flow disrupter creates a pressure differential at the fluid output port for drawing fluid out of the air-trap.

The cartridge of this embodiment can posses a ratio of the length of the short segments of the tortious flow path to the width of the flow path from about 1:2 to 1:50, preferably from about 1:4 to 1:25, and most preferably from about 1:5 to 1:10. In this embodiment, the length of the short segments of the tortious path can be from about 0.25 inches to about 1 inch in length. Likewise, the depth of the tortious flow path has a ratio of depth to length of the short segments of flow length from about 0.01:1 to 1:1, with specific depth of about 0.01 inches to about 0.25 inches.

The heat exchanger of the present invention can create the tortious path via at least one plurality of fins. Within that plurality of fins, the distance between a first and second fin can be from about 0.25 inches to about 0.5 inches.

The fluid-flow disrupter of the air-trap of the current embodiment can extend from the inner surface of the air-trap. Moreover, the purging mechanism may utilize an ultrasonic detection mechanism to monitor fluid height. Likewise, the purging mechanism may use a valve at a fluid output port and a valve at an air output port working in tandem to force air out the air output port as the volume of the fluid within the air-trap increases. Also, the valves of the purging mechanism can be controlled by monitoring mechanisms contained within a pump housing reversibly attachable to the cartridge.

In an additional embodiment of the present infusion cartridge, the device may comprise at least one pressure monitor for monitoring the pressure of fluid within the disposable cartridge as well as a bubble detector for monitoring the presence of bubbles within fluid passing through the disposable cartridge.

The heat exchanger 101, as depicted in FIG. 1, is contained within the disposable cartridge 100. The disposable cartridge is removably attached to the pump system such that once the treatment is completed, the disposable cartridge can be removed and discarded. The disposable cartridge is self-contained and once attached to the pump system need not be adjusted or manipulated. Fluid enters the disposable cartridge in the primary in-flow tube 102 which draws fluid from the fluid source. The fluid is drawn into the primary in-flow tube 102 and proceeds past a first t-junction which serves as the inflow pressure monitor 103. The inflow pressure monitor 103 is in fluid communication with a first air chamber 151. The inflow pressure monitor 103 determines the pressure of the fluid flow as it enters the pump loop 104 to allow for proper regulation of the fluid flow. The pump loop 104 interacts with a rolling or otherwise detachable pumping system. The pump loop 104 when interacting with a pumping system pushes the fluid through the disposable cartridge 100. When the fluid leaves the pump loop 104 it flows through a second t-junction which serves as the outflow pressure monitor 105. The outflow pressure monitor 105 determines the pressure of the fluid as it exits the pump loop 104 so that the flow of the fluid through the disposable cartridge 100 can be regulated.

The fluid then passes into the heat exchanger 101 via the exchanger inlet port 106 at the lower aspect of the heat exchanger. After the fluid passes through the turbulent environment established by the heat exchanger 101 it exits via the exchanger outlet port 107 located a position opposite the exchanger inlet port 106 at the upper aspect of the heat exchanger 101. At this point, the fluid for infusion has undergone its warming and the desired temperature has been reached.

The fluid exits the heat exchanger 101 via the exchanger outlet port 107 and then enters the air-trap 110 at about the mid-point along the long-axis of the air-trap 110. Fluid flows out of the air-trap 110 and through a third t-junction which serves as the out-flow bubble detector 112. The out-flow bubble detector 112 determines whether excess amounts of air have infiltrated the system. If an unacceptable level of air remains in the fluid as it flows past the out-flow bubble detector 112, the system will not allow the infusion of that fluid into the patient's body. If the fluid contains no air, or a minimal amount of air such to be acceptable, the fluid passes the out-flow bubble detector and into the patient via the primary out-flow tube 111.

Figure 3:
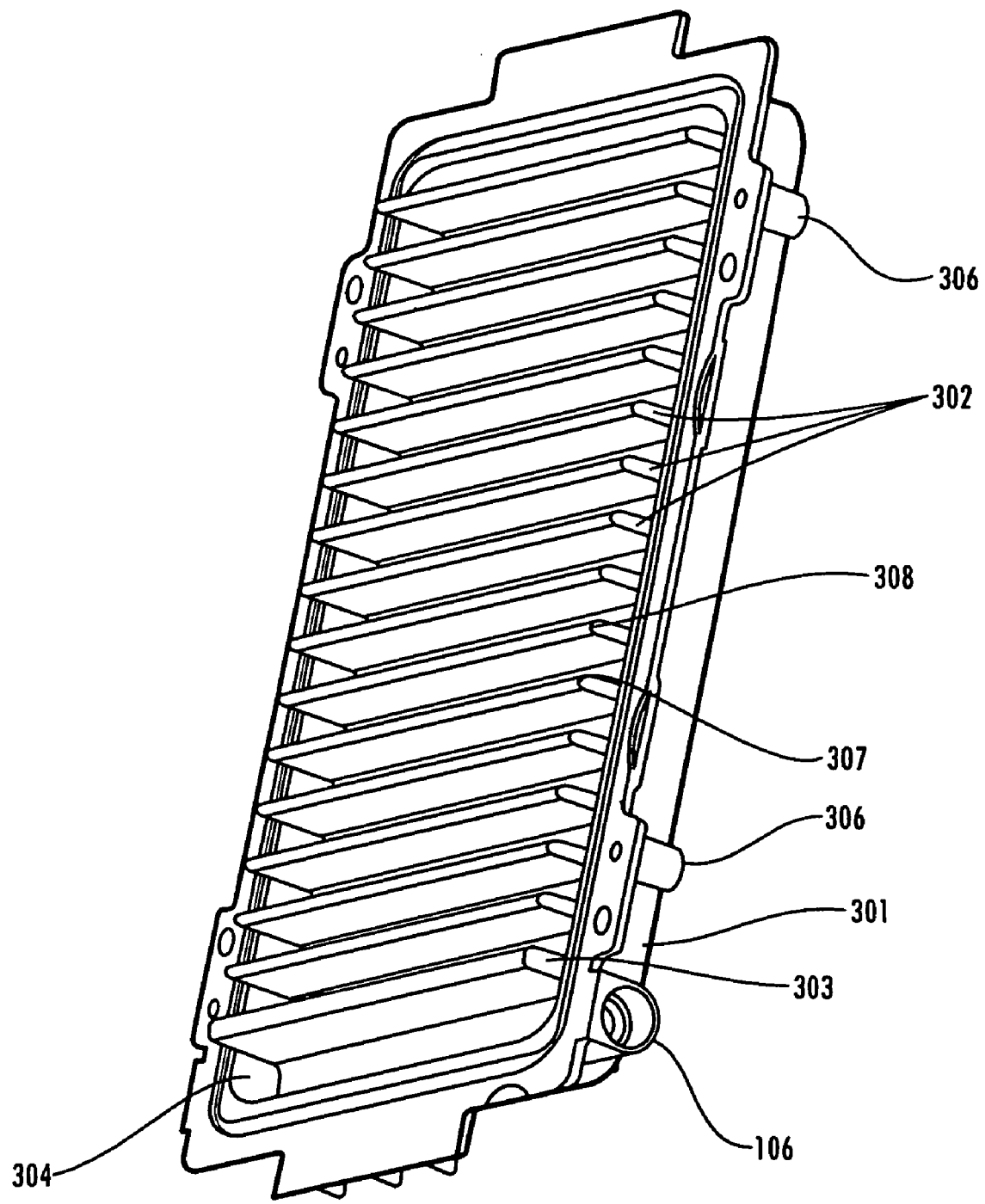
FIG. 3 shows one-half of the heat exchanger—one plurality of fins.
Figure 4:
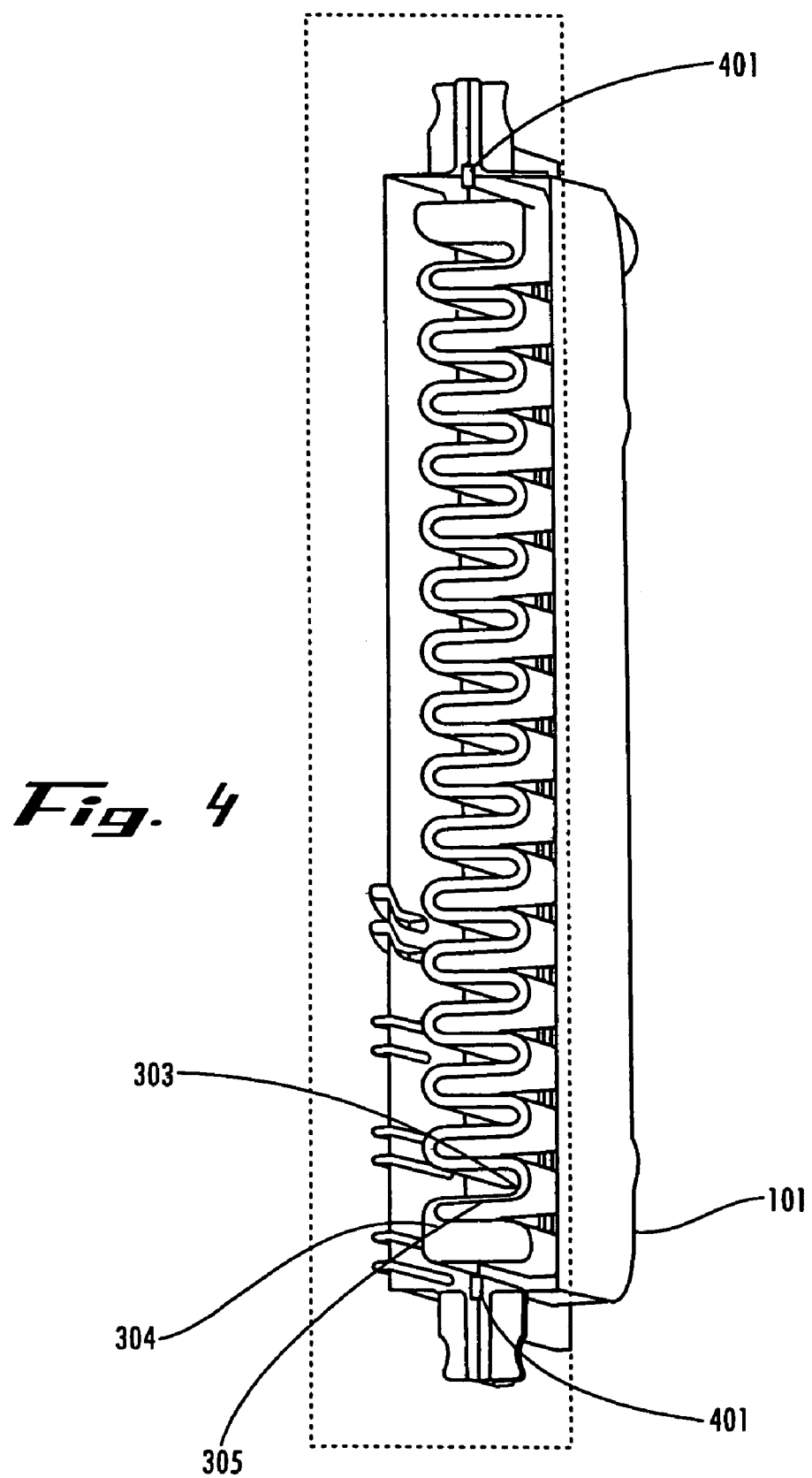
FIG. 4 is a cross-section of the heat exchanger, artificially hollowed, showing a fluid flow path in accordance with one embodiment of the present invention.

A detailed description of the heat exchanger 101 requires reference to FIGS. 3 and 4. Heat exchanger 101 can be created by two halves cast from the same mold each containing a plurality of fins. A first halve 301 is comprised of the exchanger inlet port 106 and a plurality of fins comprising a series of spaced fins 302. With the exception of a specially sized flow fin 303, each of the fins 302 are of equal size and are spaced equidistant from one another. As fluid enters the heat exchanger 101 through the exchanger inlet port 106, the fluid fills the flow cavity 304 defined by the inner walls of the heat exchanger and the flow fin 303. When in operation, the heat exchanger is oriented such that a lower aspect, where the inlet port is located, and an upper aspect, where the outlet port is located, are oriented in a vertical form forcing fluid to flow in an upwardly direction through the heat exchanger and against gravitational forces. Because of the special shape given the flow fin 303 the fluid fills the flow cavity 304 before proceeding up through the heat exchanger 101.

Using FIG. 4 to describe the flow of fluid through the heat exchanger 101, fluid enters the flow cavity 304 via the exchanger inlet port. Because of the differentially sized flow fin 303, fluid first fills the flow cavity 304 before rising over the first fin. This preliminary filling allows the fluid to fill the width of the heat exchanger and flow as a wide ribbon of fluid across the fins—opposed to a laminar flow through a long but narrow conduit. The flow fin 303 accomplishes the appropriate spreading of fluid by creating a thinner flow gap 305 between the flow fin 303 and the first of the plurality of fins of regular shape. The fluid then flows up the length of the heat exchanger 101 between the exchanger inlet port and the exchanger outlet port. As the fluid rises, it travels in wave form as a shallow but wide ribbon of fluid. The wide-flow, short linear track flow pattern created by the heat exchanger creates a turbulent flow causing increased molecular circulation within the fluid. While laminar flow within typical conduits, such as tubes, see higher molecular "turnover" in the central portion of the conduit, the turbulent flow within the heat exchanger 101 provides much more exposure of different molecules to the interior surface of the heat exchanger thereby facilitating more efficient and effective energy transfer.

Returning to FIG. 3, the other halve of the heat exchanger can be created from the same mold, wherein the exchanger inlet port 106, becomes the exchanger outlet port. Once formed, the two halves are mounted together using means known in the art, including but not limited to bolts, screws, or other mechanical means, as well as glues, cements, or other chemical means. If mechanical means are used, then fixation tabs 306 can be used to house the fixation devices.

FIG. 4, the cross-section view of the heat exchanger, further shows the seal seat 401 which provides for a space to place a seal about the circumference of the heat exchanger to increase the liquid impermeability of the heat exchanger, such as an o-ring. It should be noted that while the heat exchanger of the present embodiment is described as being formed from two identical halves the heat exchanger could be formed as a singular piece or more than two pieces. For ease in manufacture, however, two identical halves as described herein allows for the proper result through less cost.

The heat exchanger of the present invention can be formed from any number of materials: cast anodized aluminum, copper, gold, and the like. The material chosen for use in the heat exchanger of the present invention must be capable of adequate heat conduction and dispersion to ensure proper heat distribution across the surface as well as heat transfer to the fluid desired to be warmed. Thermodynamics dictates that for two materials with the same specific heat, that is the amount of heat energy required to change the temperature of the material one unit per unit of mass, the material with a greater mass will more efficiently transfer heat to the material with a lesser mass. This efficiency level is often understood as thermal capacitance—in that materials with greater thermal capacitance (i.e. mass) will retain more heat while transferring energy to the adjacent material sufficient to greatly increase the temperature of the second material without the unwanted loss of energy. Analogizing the heat exchange occurring between the heat exchanger and the infusion fluid by way of example, a material with a mass of 1.5 kg is heated to 60° C. and placed in close, direct contact with a material having a mass of 0.5 kg at a temperature of 40° C. When the heating is complete, both materials will achieve a temperature of 55° C. The energy stored by the hotter component via its increased mass allows for a better exchange of heat energy between the two materials. The selection of a material, given the special requirements of the present invention, therefore requires the consideration of the mass of the material as well as the thermodynamic properties of that material.

Figure 5:
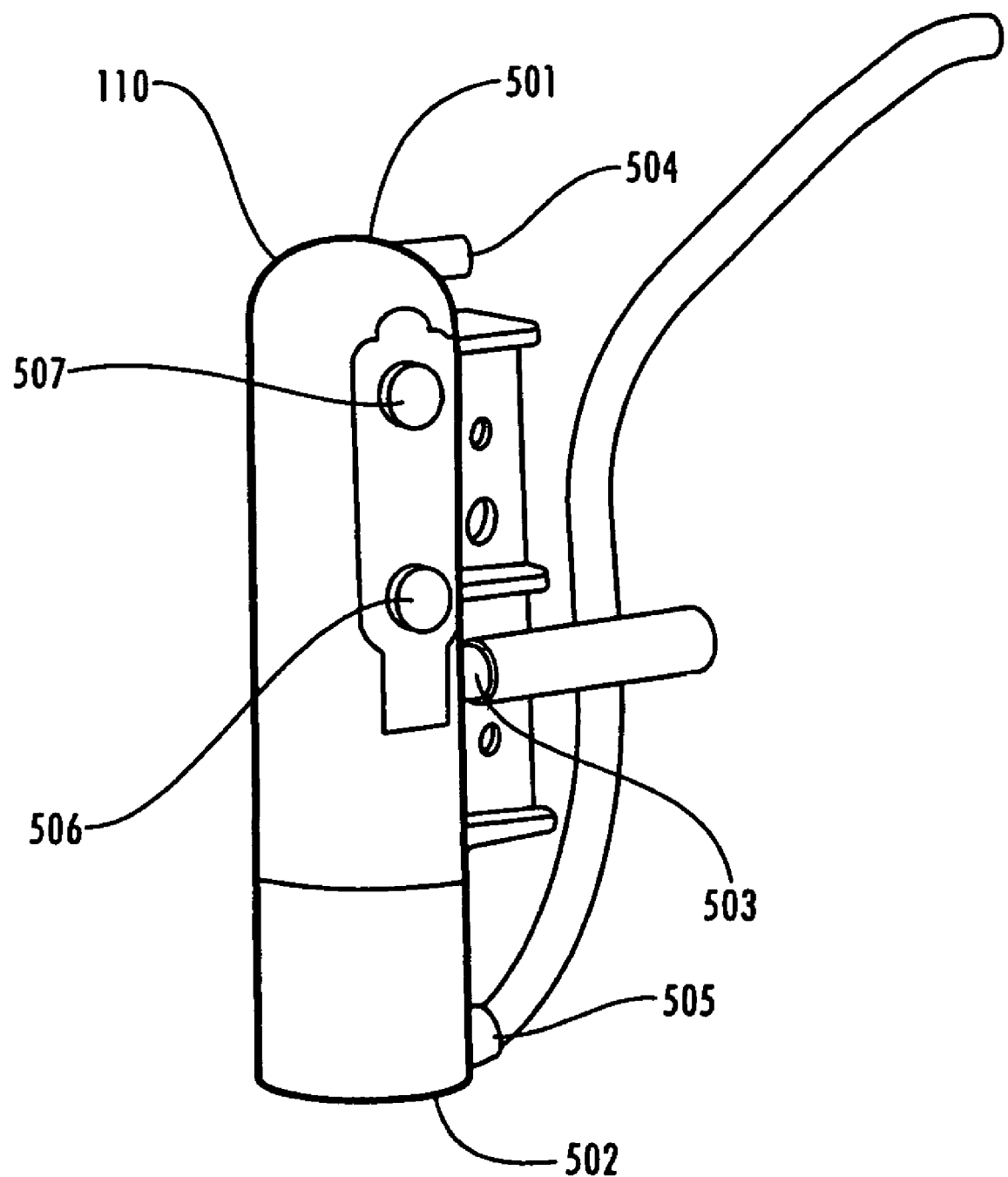
FIG. 5 is an outside view of an air-trap in accordance with the present invention.

FIG. 5 shows an enlarged view of the air-trap 110 and its connective conduits. While the air-trap is described with reference to specific shapes, it should apparent to one of skill in the art that any shape which would allow for the reversal of fluid flow direction at the fluid output port of the air-trap will allow for the monitoring and removal of air from the cartridge system. The air-trap is generally cylindrical in shape with a domed top 501 and flattened bottom 502. Fluid enters the air-trap 110 at the air-trap intake port 503 located at approximately midway along the long axis of the air-trap. Fluid enters the air-trap 110 from the heat exchanger in order to remove any air trapped or introduced into the fluid. The air to be removed may have come from failure to purge the fluid source of air before introducing it to the present invention. It is also possible that the heating of the fluid causes the release of bound gas creating bubbles which if allowed to enter the patient's body could be deleterious or even deadly. Fluid exits the air-trap 110 through the fluid output port 505 located at the bottom 502 of the air-trap.

Figure 6:
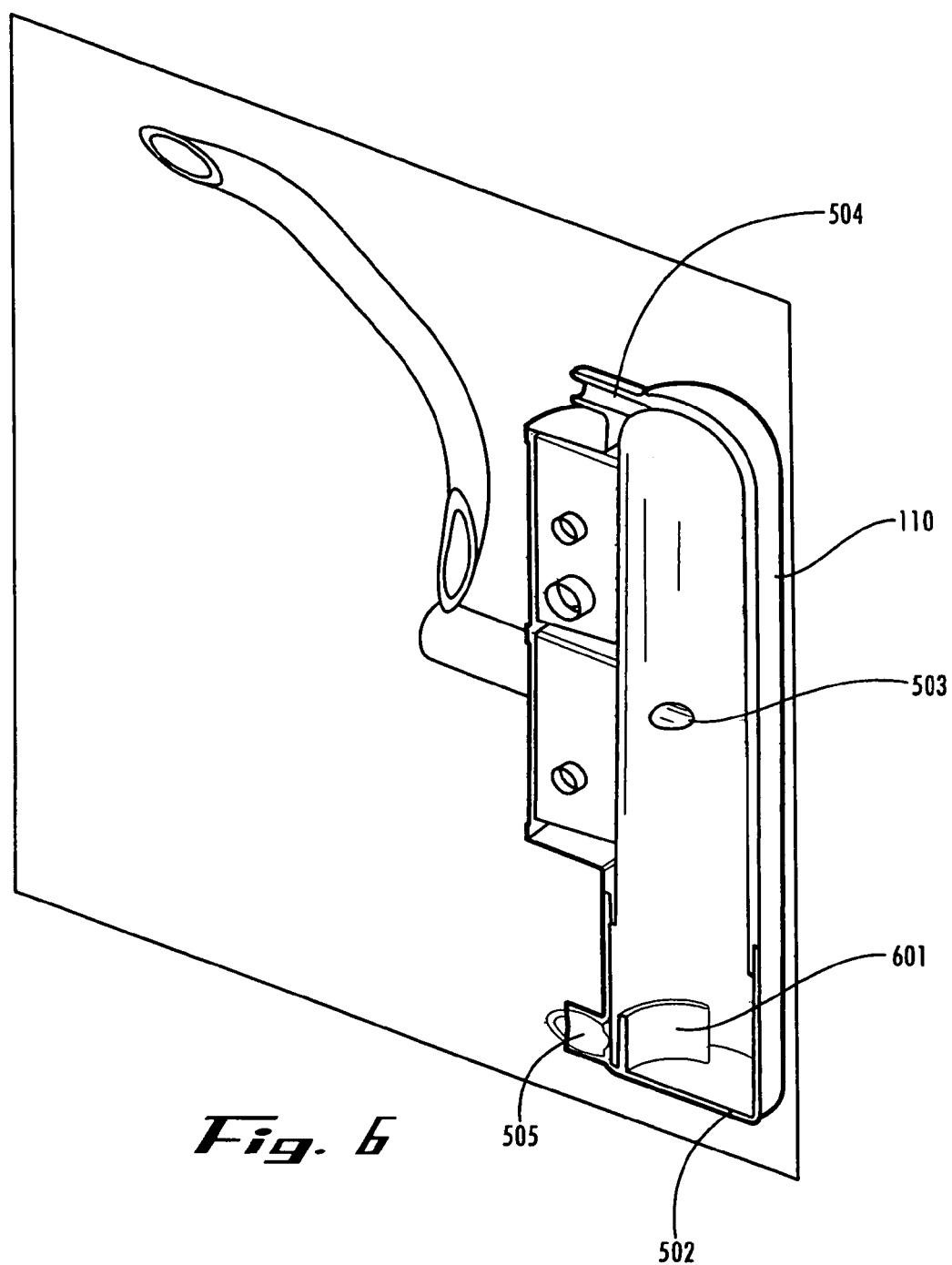
FIG. 6 is a cross-section of an air-trap in accordance with the present invention.

FIG. 6 depicts a cross-section of the air-trap 110. In this view, one can see the air-trap intake port 503 as it interfaces with the air-trap. The air-trap intake port 503 is smoothed to the inside wall of the air-trap and is positioned off of the mid-line of the long axis of the air-trap. This position of the air-trap intake port 503 relative to the mid-line of the long axis of the air-trap causes the fluid being introduced to the air-trap to flow about the cylindrical form of the air-trap in a clockwise direction as the fluid fills and continues to enter the air-trap. This flow pattern creates a vortex within the air-trap pulling air downward toward the fluid output port. At the bottom 502 of the air-trap there is located a flow disrupter 601 which is positioned adjacent to the fluid output port 505. The flow disrupter can extend from the inner wall of the air-trap or the inner wall of the bottom 502 of the air-trap. As the fluid, which is traveling clockwise about the air-trap, flows across the flow disrupter 601, a differential in pressure at the fluid output port 505 is created drawing the liquid out of the air-trap and allowing the air or gas bubbles to flow upward along the long-axis of the air-trap.

Returning to FIG. 5, the level of fluid within the air-trap is continuously monitored while the infusion device is being operated. When the level of fluid in the air-trap 110 drops below the lower level sensor 506 a valve located at or about the fluid output port 505 closes. At approximately the same time that the valve located at or about the fluid output port 505 closes, a valve located at or about the air output port 504 opens. With the fluid output port 505 closed, fluid entering the air-trap 110 forces any air present in the air-trap up the long axis of the air-trap. Because the air output port 504 is open, any air within the air-trap is forced out of the air-trap and into the air output tube 108 shown in FIG. 1. When the level of fluid in the air-trap 110 rises above the upper level sensor 507, the valve at the air output port 504 closes. At approximately the same time that the valve at the air output port 504 closes, the valve at the fluid output port 505 opens again. With the fluid output port 505 open, fluid flow out to the patient via the primary out-flow tube 111 is restored.

The air-trap embodied by the present invention is capable of functioning at varying inclinations and orientations. The cylinder formed by the air-trap is between 3 inches and 10 inches in height, preferably between 3.5 inches and 7 inches, and most preferably between 4 inches and 6 inches. The diameter of the air-trap cylinder is between 0.5 inches and 2 inches, preferably 0.625 inches and 1.5 inches, and most preferably 0.75 inches and 1.25 inches. The air-trap is able to properly remove air from the fluid as it passes through even when the air-trap is tilted off its vertical axis up to 45°.

Figure 7:
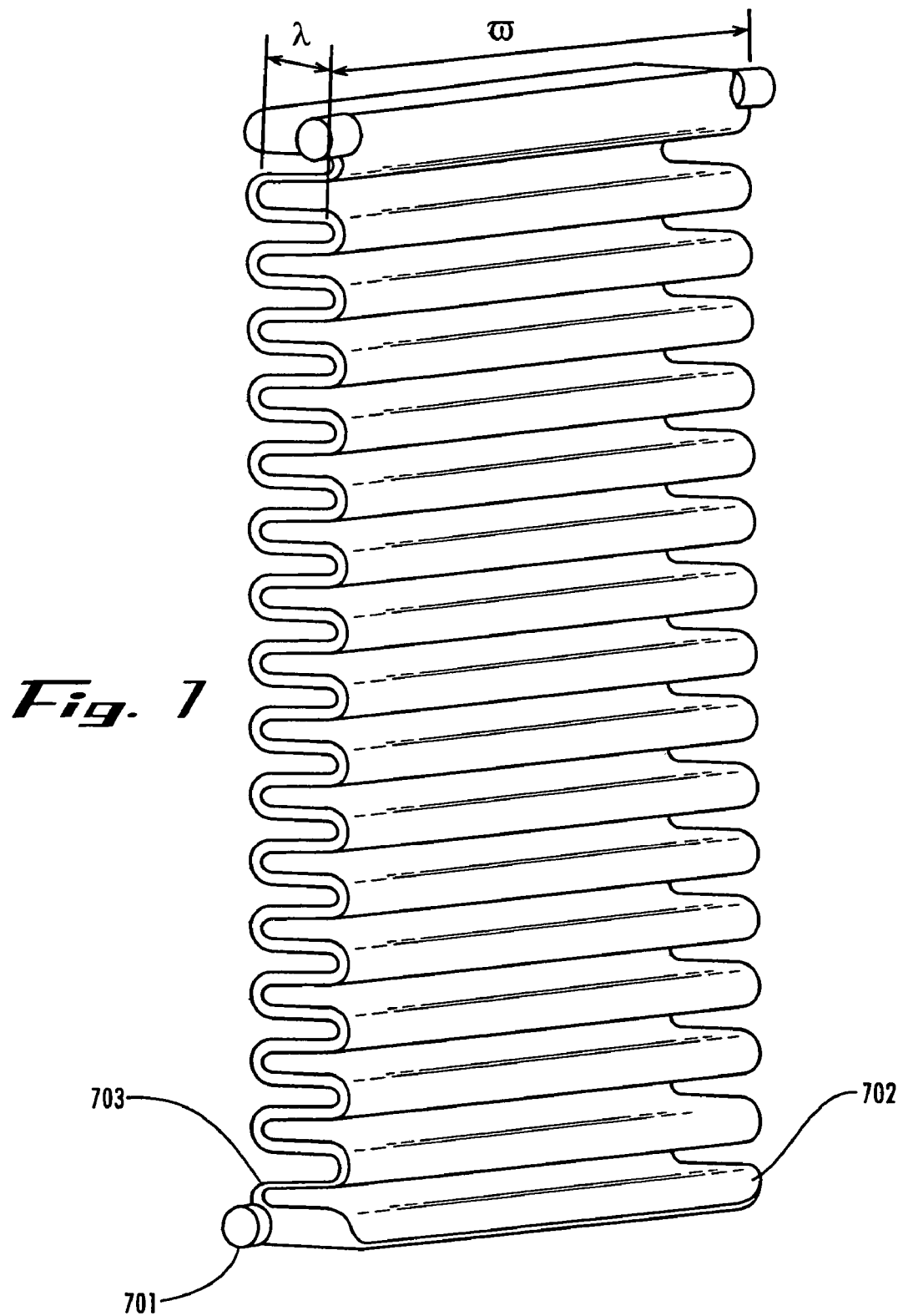
FIG. 7 shows the shape of fluid that would fill a heat exchanger in accordance with the present invention.
Figure 8:
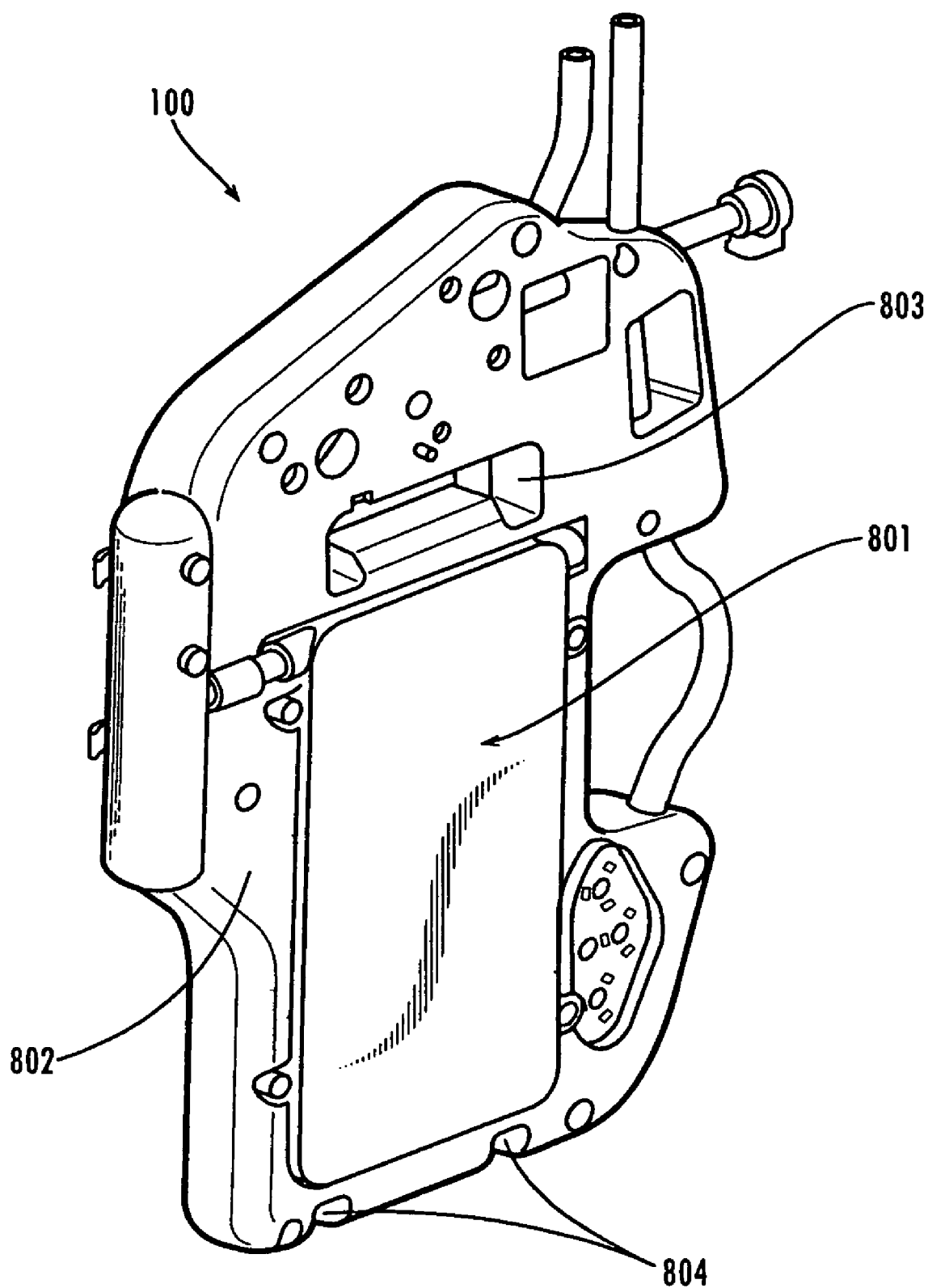
FIG. 8 shows a disposable cartridge of one embodiment of the present invention.

As discussed above, efficient transfer of heat from the heating element to the fluid to be warmed heavily impacts the present invention. The present invention's use of a wide flow, short linear travel flow pattern allows for a more turbulent flow with an extremely large contact area. The contact area being described is the area of interface between the heat exchanger and the fluid passing through. Described as a ribbon of fluid, the fluid traveling through a heat exchanger made in accordance with the present invention will flow in very short linear distances along the short segments of linear distance but will instead be proportionately wider. In fact, the cavity created for fluid flow through the heat exchanger is wider than it is long, and longer than it is deep thereby creating a tortious ribbon shape for the fluid to pass through. FIG. 7 is a representation of the fluid flowing through the heat exchanger 100. The fluid flow of FIG. 7 first is shown as having filled the exchanger inlet port as the inlet fluid 701. The fluid then fills the flow cavity as cavity fluid 702. The fluid then flows up the heat exchanger first through the smaller gap created by the flow fin indicated as the first restricted flow 703. It should be noted that linear flow distance $\lambda$, defined by the height of the fins and representing the short segments of flow length, is less than the flow width $\omega$. The ratio between the linear flow distance $\lambda$ and the flow width $\omega$ can be from about 1:2 to 1:50, preferably from 1:4 to 1:25, and most preferably from 1:5 to 1:10. It is the ratio between the linear flow distance and the flow width which creates the ribbon-like flow pattern depicted in FIG. 7. By having such a short linear flow, the fluid flows through the heat exchanger with more turbulence than a typical long linear flow serpentine path. The introduction of turbulence in the fluid avoids the laminar type flow that such a serpentine flow path may create. As opposed to merely the molecules within the central portion of the fluid flow, that is those molecules not located directed at the interface, changing over faster than the molecules at the interface, the turbulent flow created by the present invention exposes more fluid molecules to the interface which allows for an enhanced heat transfer. Likewise, this turbulent flow creates more contact between the molecules within the fluid flowing through the heat exchanger. With more contact between the molecules within the fluid, more heat exchange and transfer can occur driving the efficient exchange of heat from the exchanger to the fluid to be delivered to the patient.

A heat exchanger made in accordance with the present invention creates this turbulent flow path and maintains it as the fluid flows over the fins. The fins, as depicted in FIG. 3, create one-half of the flow path for the fluid to follow. The fins on the same side of the heat exchanger are evenly sized and spaced, that is the distance between a first fin 307 and a second fin 308 is the same across to overall span of the heat exchanger. For the purposes of heat transfer involving a fluid flowing in the heat exchanger, the distance between a first and second fin of the same plurality of fins can be from 0.25 inches to 0.5 inches, preferably from 0.35 inches to 0.45 inches, and most preferably from 0.37 inches to 0.43 inches. The length of the fins on one-half of the heat exchanger dictates the linear flow distance. The length of the fins can be from about 0.25 inches to 1.0 inches, preferably from 0.5 inches to 0.8 inches, and most preferably from 0.6 inches to 0.7 inches. The flow path also contains a depth element created by the separation distance between the top of the fins in a first plurality of fins and the valley between two fins in a second plurality of fins. The flow path can have a depth of about 0.01 inches to 0.25 inches, preferably 0.03 inches to 0.125 inches, and most preferably 0.04 inches to 0.110 inches. The width of fins can be from 3 inches to 6 inches, preferably 3.5 inches to 5 inches, and most preferably 4 inches to 4.5 inches.

Transfer of heat energy to the heat exchanger occurs at the exposed portion of the heat exchanger, that is the portion not covered or contained within the disposable cartridge. The flat plate 801 of the heat exchanger is visible in FIG. 8 exposed from the housing 802 of the disposable cartridge 100. The disposable cartridge 100 is removably fixed to the pump system via a first attachment region 803 and a second attachment region 804. The attachment regions allow the disposable cartridge to be affixed to the pump system securely and tightly. It is extremely important that the flat plate 801 of the heat exchanger be located as close to the heating element or platen as possible. It is equally important and difficult to ensure that the flat plate 801 of the heat exchanger is uniformly close to the heating element or platen. Even known smooth materials, when dealing with solids, are rarely completely in contact when considered at a microscopic level. Therefore, flat plate 801 should be as reasonably uniform and smooth as possible in order to achieve as much surface area contacting the heating element or platen. The surface area of the flat plate 801 which contacts the heating element or platen can be from about 20 square inches to about 100 square inches, preferably from about 25 square inches to about 50 square inches, and most preferably from about 30 square inches to about 45 square inches. Likewise, the pressure exerted onto the disposable cartridge 100 to hold the flat plate 801 in close contact with the heating element or platen must increase if the surface of the flat plate 801 and the heating element or platen are not smooth. If the flat plate 801 and the heating element or platen are positioned immediately next to one another, it is considered that an air interface exists between the two surfaces. Because while the surfaces will be extremely close and pressure will be exerted on the flat plate 801 such to press the two surfaces together, gaps between the surfaces will remain. It is therefore possible to reduce these gaps by coating the heating element or platen which contacts the flat plate 801 of the heat exchanger with a thermal pad which conforms and fills the voids between the surfaces with a material that is a better heat conductor than air yet allowing a reasonable contact pressure to be used. If air serves as the interface between the surface of the flat plate 801 of the heat exchanger and the heating element or platen, then greater pressure must be exerted on the system in order to achieve an efficient transfer of heat energy. Using a material which fills the gaps and is a better heat conductor than air allows the system to be established with a lesser and more reasonable pressure applied to the surface interface.

Example

Figure 2A:
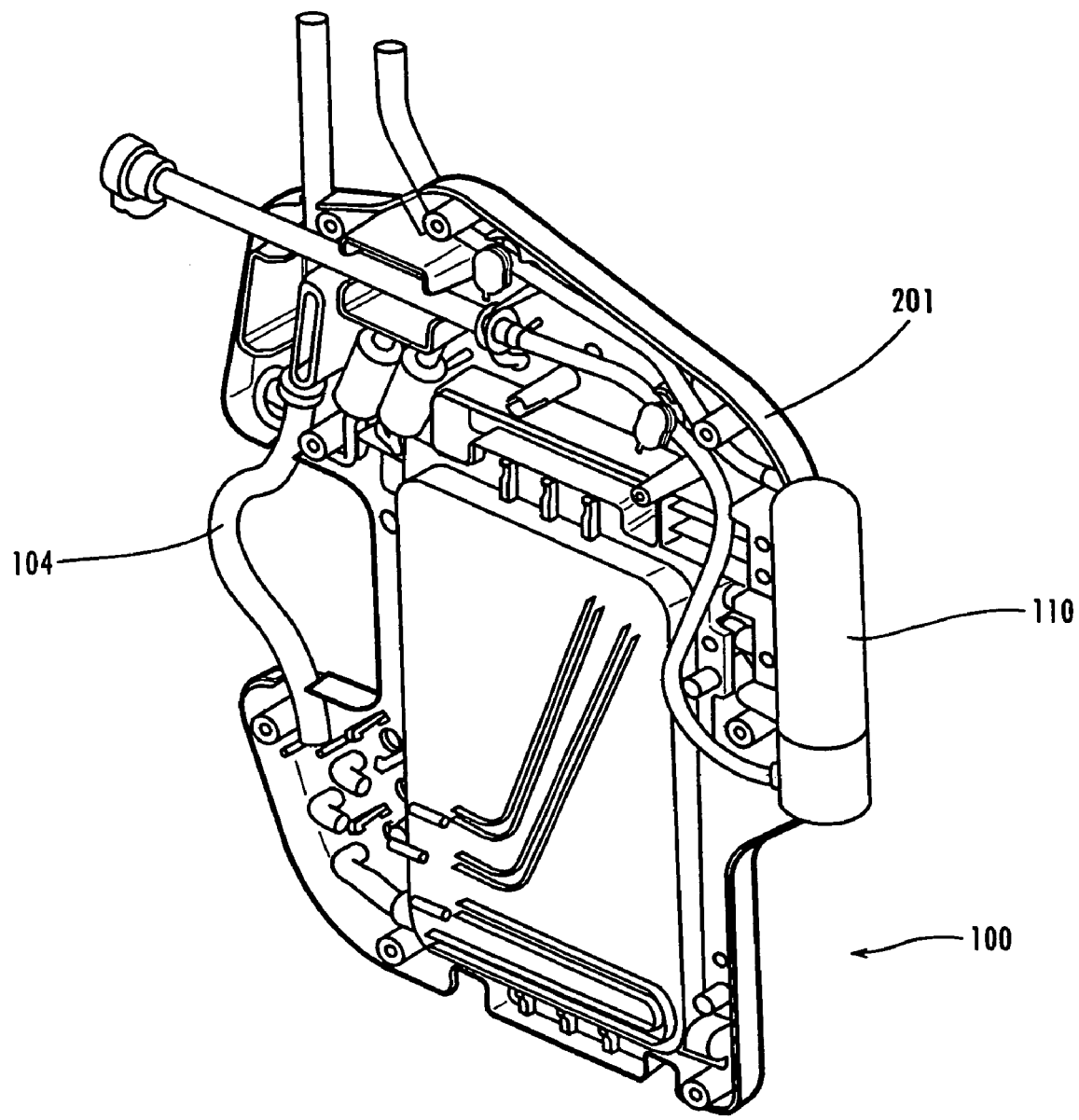
FIG. 2a shows a different orientation of the disposable cartridge in accordance with the present invention (near cover of disposable removed).
Figure 2B:
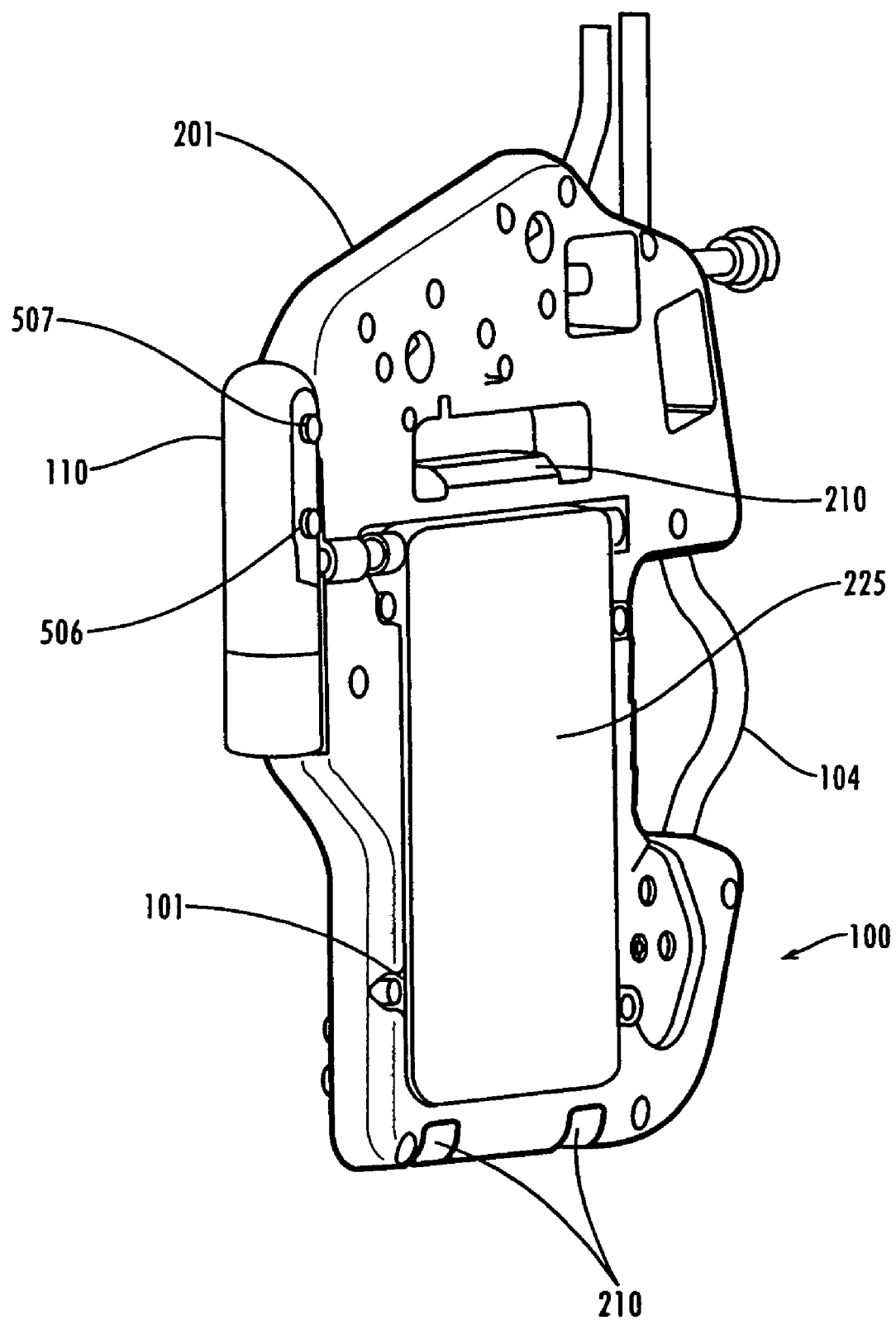
FIG. 2b shows the side of the disposable cartridge of one embodiment of the present invention which abuts the pump housing.
Figure 2C:
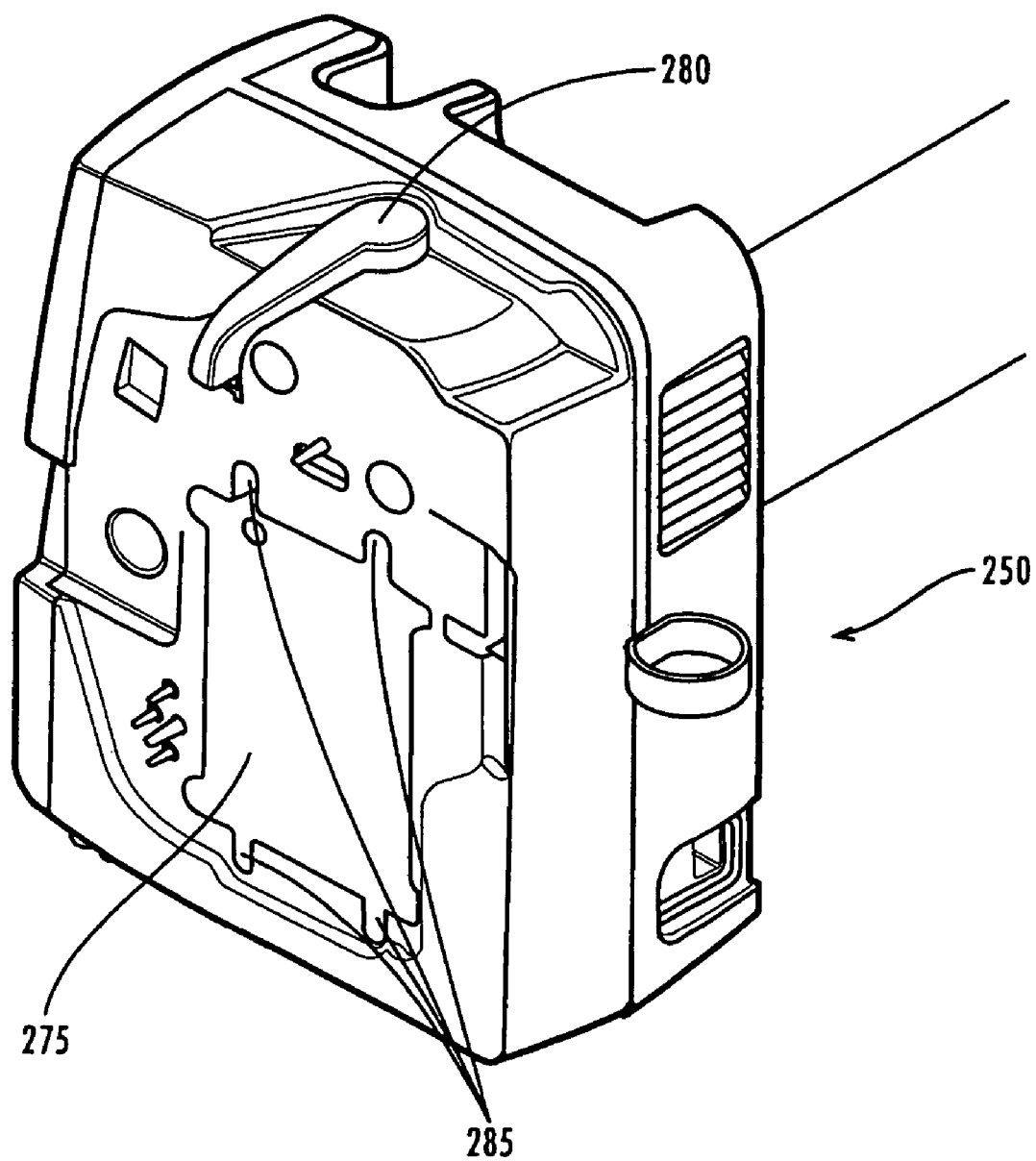
FIG. 2c shows the pump housing with exposed platen embodying one aspect of the present invention.

An infusion system under the present invention in shown in FIG. 2*a-c*. The disposable cartridge is shown with half of its outer cover removed in FIG. 2*a*. For orientation purposes, the air-trap 110 is visible extending out of the outer cover 201 at the right-hand portion of the figure. The outer cover of the disposable is made of sturdy polymeric material. FIG. 2*b* shows the side of the disposable cartridge which will contact the pump housing 250 shown in FIG. 2*c*. Again for orientation, the air-trap 110 is shown in FIG. 2*b* at the left-hand portion of the figure extending out from the outer cover 201. The exposure surface 225 of the heat exchanger 101, which will be in contact with the platen of the pump system, is shown in FIG. 2*b*. FIG. 2*c* shows the pump housing which contains the roller pump to interact with the pump loop 104. FIG. 2*c* also shows the platen 275 which provides the heat energy to the heat exchanger contained within the disposable cartridge. All elements of this Example are in fluid connection with one another.

Engaging handle 280 allows the user to reversibly attach the disposable 100 to the pump housing 250 by clamping or other locking mechanisms that extend from lock housings 285 located about the platen 275. When engaging handle 280 is manipulated, the clamping or other locking mechanisms contained within the lock housings 285 extend and engage the disposable 100 at attachment points 210 located about the exposure surface 225 of the heat exchanger 101. When engaged, the force provided to couple the exposure surface 225 of the heat exchanger 101 to the platen 275 is from about 170 pounds to 230 pounds with the normal force being about 200 pounds. Located between the exposure surface 225 and the platen 275 is a conductive material, or silpad, which allows for extremely close and uniform contact between the platen and the heat exchanger. The material chosen as the silpad is a silicone-based pad, Chomerics T500®, supplied by Chomerics, located in Woburn, Mass. The silpad allows for better heat transfer from the platen 275 to the heat exchanger 101 than an interface of air would allow. In this Example, the silpad is about 0.02 inches thick, give or take 0.005 inches, and covers the entire platen. Moreover, in this Example the surface area of the flat plate 801 which contacts the heating element or platen is about 35 square inches.

For the purposes of this Example, the fluid being infused into the patient is blood. The fluid entering the pump system embodied in this Example is 20° C. The rate at which infusion is conducted is 1000 ml/min. The pump contained within the pump housing in this Example is capable of pumping fluid at a rate of 10 ml/hr to 1200 ml/min.

Once the cartridge is engaged, the rolling pump contained within the pump housing will apply pumping pressure to the pump loop 104 causing fluid to flow from a fluid source through the cartridge sufficient to infuse at 1000 ml/min. Again referring to FIG. 1, the blood is drawn into the primary in-flow tube 102 and proceeds past a first t-junction which serves as the inflow pressure monitor 103. The inflow pressure monitor 103 is in fluid communication with a first air chamber 151. The inflow pressure monitor 103 determines the pressure of the blood flow as it enters the pump loop 104 to allow for proper regulation of the blood flow.

The inflow pressure monitor 103 monitors negative pressure in the event that fluid remains within the disposable cartridge but is not flowing in the direction of the patient. Such a circumstance could arise if the fluid source bag collapses yet fluid remains in the cartridge. If the pressure at the inflow pressure monitor 103 falls below 1 mmHg, then the pump will stop pumping.

When the blood leaves the pump loop 104 it flows through a second t-junction which serves as the outflow pressure monitor 105. The outflow pressure monitor 105 determines the pressure of the blood as it exits the pump loop 104 so that the flow of the blood through the disposable cartridge 100 can be regulated. The outflow pressure monitor measures the pressure of the fluid proceeding through the cartridge. Here the pressure monitors for flow blockage so that when the pressure exceeds 500 mmHg the pump will shut down to avoid damage.

The blood then passes into the heat exchanger 101 via the exchanger inlet port 106. The heat exchanger 101 of this Example is created from two halves as depicted in FIG. 3. The two halves are created from the same mold such that inverting one mold and fixing the two together creates the heat exchanger. The material used in the creation of the heat exchanger of this Example was anodized aluminum. The use of this material accomplishes the goal of the present invention by creating a large mass differential between the heat exchanger and the fluid, blood, to be warmed. The heat conduction ability of the anodized aluminum allows for excellent dissipation of heat energy across the heat exchanger. The anodized surface of the aluminum creates a biological inert surface such to prevent either the reaction with, or adsorption of, biological material while the blood or other fluid passes across it. In the present Example, dealing with blood, protein adsorption to the surface of the material may generate a trigger to the clotting cascade. The adsorbed proteins to the inner surface of the heat exchanger, even if they do not trigger the clotting cascade, can become degraded and detach. Once detached from the surface of the heat exchanger, these degraded or denatured proteins may react with other proteins or the cells contained within the blood in deleterious manners. The anodized inner surface of the heat exchanger thus prevents damage from occurring to the blood as it passes through the heat exchanger.

When a cartridge according to the present invention is used, the effective exchange of heat from the heat exchanger to the fluid being infused achieve the appropriate rise in temperature of the fluid without having to expose the fluid to a temperature of 45° C. or greater. Instead of having regions of varied temperature to which the blood or fluid is exposed, the heat exchanger's constant temperature allows for more efficient transfer of heat energy to the blood. At a flow rate of 1000 ml/min, achieving a fluid exit temperature of 37° C. means never having to expose the blood to a temperature of 45° C. which could be deleterious to the fluid being infused. In fact, using anodized aluminum yielded a 95-96% efficiency in transferring heat energy to blood sufficient to generate a 17° C. rise in temperature.

Once the blood enters the heat exchanger, the blood fills the flow cavity before proceeding to traverse the entirety of the heat exchanger. The blood fills the flow cavity first because of the narrower flow area created by the flow fin which defines the flow cavity. By creating a smaller flow path to flow over the first fin, as depicted in FIG. 7, the blood will not traverse the long axis of the heat exchanger before it fills the flow cavity causing the flow pattern across the heat exchanger's fins to be a wide ribbon-like shape.

The fins used in the heat exchanger described in FIGS. 2a-c are spaced at about 0.4 inches apart. The depth of the flow path created by the separation of the two pluralities of fins is about 0.08 inches. The fins are about 4.3 inches wide and 0.62 inches in height. This creates a ratio of linear flow distance to width of about 1:7. The flow fin 303, as seen in FIG. 3, is wider than the remainder of fins across the heat exchanger. That increased width of the flow fin 303 creates a narrower flow path at that fin when the two halves of the heat exchanger are connected. In this Example, the width of the flow path created by the flow fin 303 is about 0.03 inches. Given that the blood flowing through the heat exchanger in this Example will travel along a path of least resistance, the flow cavity 304 will fill before the blood travels past the flow fin 303. The blood then travels over the fins which creates a turbulent flow pattern for the blood as it travels through the heat exchanger. This turbulent flow ensures an increased exposure of more molecules within the blood fluid to the heat exchanger thereby increasing the efficient transfer of heat energy.

Once the blood flow reaches the top of the heat exchanger it exits the via the exchanger outlet port 107 located a position opposite the exchanger inlet port 106 of the heat exchanger 101. At this point, the fluid for infusion has undergone its warming and the desired temperature has been reached. The blood then enters the air-trap 110 at a location approximately midway between the top and bottom of the long-axis of the air-trap 110. In this Example, the air-trap is about 4.2 inches along its long, vertical axis and about 1 inch in diameter. The air-trap intake port 503 is located about 2.1 inches from the bottom of the air-trap (see FIG. 6). As the blood passes through the air-trap intake port, the blood travels in a clockwise direction as the blood fills the air-trap. This clockwise flow of blood creates a vortex of fluid in the air-trap. The fluid flow disrupter 601, which in this example extends from the interior surface of the bottom of the air-trap up about 0.5 inches, creates a sufficient pressure differential at the fluid output port 505 to draw the blood out and not any trapped air.

Air may become trapped in the blood in this Example via several mechanisms. Through spiking the blood as it is attached to the pump system for infusion, in essence failing to properly purge the source of the blood before attachment to the system. Also, the heating of the fluid itself can cause the release of stored gas within the blood which may be deleterious if introduced into the patient.

As the amount of air in the air-trap 110 increases, the level of blood in this Example lowers within the air-trap. When the blood is below the lower level sensor 506, which in this Example is an ultrasonic sensor, the valve at the fluid output port 505 closes. When the valve at the fluid output port 505 is closed, the valve at the air output port 504 located at the top of the air-trap is open. This increases the blood volume in the air-trap forcing air out of the air output port 504. The ultrasonic sensors are located in the pump housing 250. The ultrasonic sensors utilize silicon buttons attached to the air-trap at the lower level sensor 506 and upper level sensor 507 in order to effectively monitor the level of fluid within the air-trap. When the level of blood rises above the upper level sensor 507, also an ultrasonic sensor, the valve at the air output port 504 closes. At approximately the same time that the valve at the air output port closes, the valve at the fluid output port 505 opens and blood exits the air-trap and proceeds toward the patient.

In this Example, the fluid then passes through a third pressure monitor which controls the overall flow within the cartridge based on pressure. If there is blockage, and the pressure begins to rise, this pressure monitor will try to keep the pressure within an acceptable range which can be between 100 and 300 mmHg. If the pressure at this pressure monitors rises above 500 mmHg the pump will shut down.

In the present Example, however, before blood reaches the patient it passes through the out-flow bubble detector 112 (see FIG. 1). The out-flow bubble detector analyzes the blood on its way to the patient to determine that the air-trap removed potentially deleterious air from the system. The bubble detector to this Example uses an ultrasonic sensor which sends a signal across the tube. Any air bubbles present in the system will attenuate the signal. The system will shut the pump down if bubbles as small as 30 to 50 µL are detected. The system is able to detect bubbles of this size at the maximum flow rate of 1200 ml/min.

What is claimed is:

1. An air-trap comprising upper and lower aspects defining a longitudinal axis extending centrally therebetween, an upper fluid input port formed in an exterior side wall of the air-trap in the upper aspect, wherein fluid enters the air-trap from the upper fluid input port at an axis orthogonal to the longitudinal axis, a lower fluid output port positioned off center from the longitudinal axis, a lower fluid flow disrupter positioned off-center from the longitudinal axis, proximate the lower fluid output port, and between the longitudinal axis and the lower fluid output port, and an upper air output port, wherein either the lower fluid output port or the upper air output port is selectively open in operation.

2. The air-trap of claim 1 wherein the air-trap is taller than wide.

3. The air-trap of claim 1 further comprising an ultrasonic detection mechanism to monitor fluid volume in the air-trap.

4. The air-trap of claim 1 further comprising a valve at the fluid output port and a valve at the air output port working in tandem to force air out the air output port as the volume of the fluid within the air-trap increases, to a pre-determined level.

5. The air-trap of claim 1 wherein the air-trap effectively removes air when moved off vertical axis up to 45°.

6. The air-trap of claim 1, wherein the upper fluid port is operable to introduce fluid into the air-trap to permit a circular flow of the fluid.

7. The air-trap of claim 1, wherein the upper fluid port is operable to introduce fluid into the air-trap to permit a circular flow of the fluid, and wherein the circular flow of the fluid at the fluid flow disrupter is disrupted to create a pressure differential proximate the lower fluid output port to draw the fluid into the lower fluid output port.

8. The air-trap of claim 1, wherein the upper fluid input port is oriented to direct fluid into the air-trap in a direction off of the longitudinal axis.

9. The air-trap of claim 1, wherein the longitudinal axis is a first longitudinal axis, and wherein the lower fluid flow disrupter is positioned between the first longitudinal axis and a second longitudinal axis parallel to the first longitudinal axis and extending through the fluid output port.

10. A cylindrical air-trap for removing air from fluid comprising an upper and lower aspect defining a longitudinal axis extending centrally therebetween, an upper fluid input port formed in an exterior side wall of the air-trap in the upper aspect, wherein fluid enters the air-trap from the upper fluid input port at an axis orthogonal to the longitudinal axis, a lower fluid output port positioned off-center from the longitudinal axis, an upper air output port, and a fluid flow disrupter positioned off center from the longitudinal axis, proximate the lower fluid output port, and between the center of the longitudinal axis and the lower fluid output port, wherein the air-trap creates a vortex of fluid introduced via the fluid input port and the fluid flow disrupter creates a pressure differential at the fluid output port for drawing fluid into the lower fluid output port.

11. The air-trap of claim 10 wherein the fluid flow disrupter extends from the inner surface of the lower aspect of the air-trap.

12. The air-trap of claim 10 further comprising an ultrasonic detection mechanism to monitor fluid height.

13. The air-trap of claim 10 further comprising a valve at the fluid output port and a valve at the air output port working in tandem to force air out the air output port as the volume of the fluid within the air-trap increases.

14. The air-trap of claim 10 wherein the air-trap effectively removes air when moved off vertical axis up to 45°.

15. The air-trap of claim 10, wherein the upper fluid port is operable to introduce fluid into the air-trap to create the vortex fluid.

16. The air-trap of claim 10, wherein the upper fluid input port is oriented to direct fluid into the air-trap in a direction off of the longitudinal axis.

17. The air-trap of claim 10, wherein the longitudinal axis is a first longitudinal axis, and wherein the fluid flow disrupter is positioned between the first longitudinal axis and a second longitudinal axis parallel to the first longitudinal axis and extending through the fluid output port.

18. An air-trap comprising upper and lower aspects defining a longitudinal axis extending centrally therebetween, an upper fluid input port formed in an exterior side wall of the air-trap, wherein fluid enters the air-trap from the upper fluid input port at an axis orthogonal to the longitudinal axis, a lower fluid output port positioned off-center from the longitudinal axis, a fluid flow disrupter positioned off-center from the longitudinal axis, proximate the lower fluid output port, and between the longitudinal axis and the lower fluid output port, and an upper air output port.

* * * * *